US 6,530,920 B1

(12) United States Patent
Whitcroft et al.

(10) Patent No.: US 6,530,920 B1
(45) Date of Patent: *Mar. 11, 2003

(54) LASER TREATMENT COOLING HEAD

(75) Inventors: Ian Andrew Whitcroft, Huron, SD (US); Richard Anthony McMahon, Cambridge (GB)

(73) Assignee: Coolanalgesia Limited, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/673,109

(22) PCT Filed: Apr. 9, 1999

(86) PCT No.: PCT/GB99/01102

§ 371 (c)(1),
(2), (4) Date: Feb. 14, 2001

(87) PCT Pub. No.: WO99/52594

PCT Pub. Date: Oct. 21, 1999

(30) Foreign Application Priority Data

Apr. 9, 1998 (GB) .............................................. 9807789
Apr. 9, 1998 (GB) .............................................. 9807793

(51) Int. Cl.$^7$ ............................................. A61B 18/02
(52) U.S. Cl. .................................. 606/13; 606/9; 606/10
(58) Field of Search .................... 606/9, 1–20; 607/89

(56) References Cited

U.S. PATENT DOCUMENTS

| 4,733,660 | A | * | 3/1988 | Itzkan | 606/9 |
| 5,735,844 | A | * | 4/1998 | Anderson et al. | 606/9 |
| 5,814,040 | A | * | 9/1998 | Nelson et al. | 606/9 |
| 5,830,208 | A | * | 11/1998 | Muller | 606/9 |
| 6,235,015 | B1 | * | 5/2001 | Mead et al. | 606/9 |
| 6,264,649 | B1 | * | 7/2001 | Whitcroft et al. | 606/9 |
| 6,273,884 | B1 | * | 8/2001 | Altshuler et al. | 606/9 |

* cited by examiner

Primary Examiner—Roy D. Gibson
Assistant Examiner—Henry M. Johnson, III
(74) Attorney, Agent, or Firm—Dykema Gossett PLLC

(57) ABSTRACT

A cooling head for attachment to a skin treatment laser has a metal body with a mount at one end for attachment to a laser head to secure the metal body to the head. A cooling surface at the other end is for application to a patient's skin and has an aperture therethrough. A bore extends from the mount through the body to the aperture in the cooling surface to allow a laser beam to be passed therethrough to a treatment area of the patient's skin. An extraction port enables removal of debris from the treatment area and for connection to a vacuum source. An optically transparent window is disposed in the body to allow the treatment area to be viewed. A cooling means (liquid flow heat exchanger, Peltier device) enables heat removal from the body in use in order to cool the cooling surface. A method of skin treatment employs the cooling head to cool the area surrounding the treatment area to reduce pain and protect the skin of the patient.

24 Claims, 8 Drawing Sheets

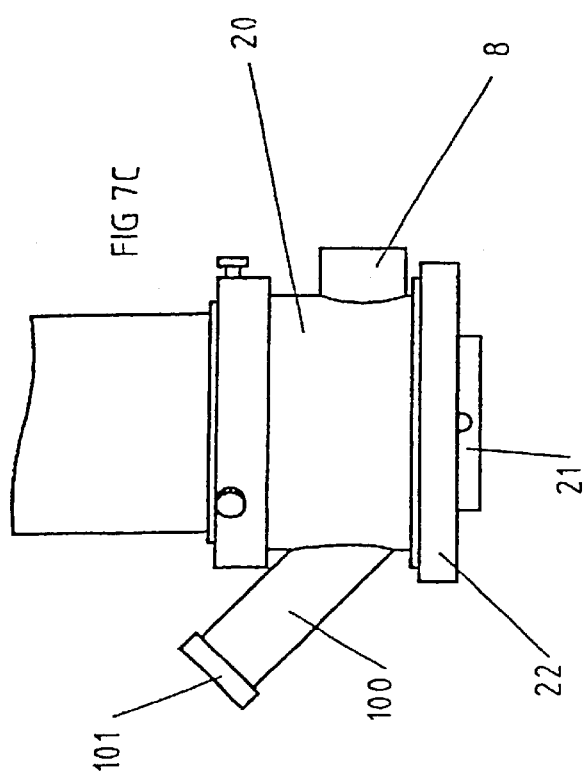
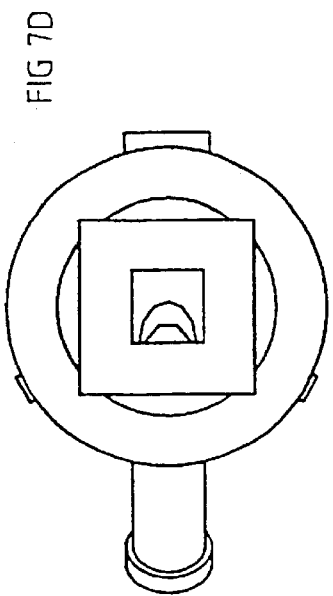
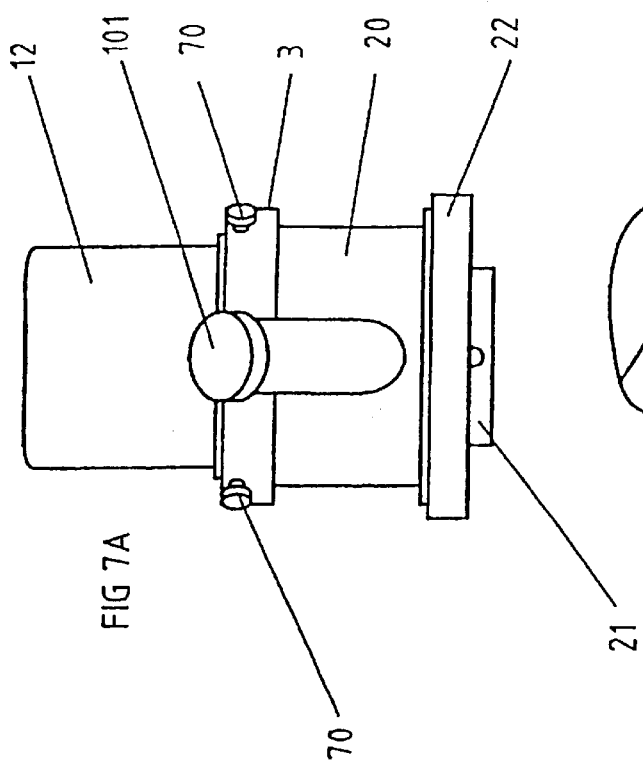
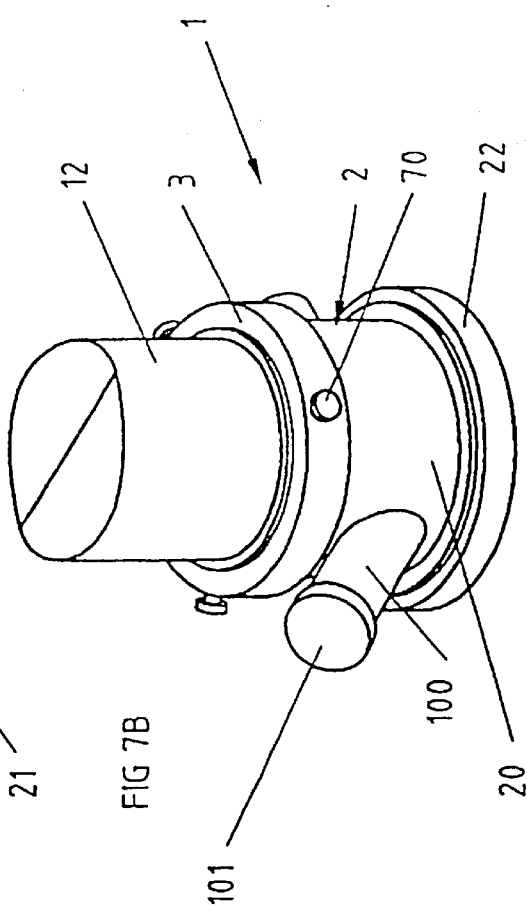

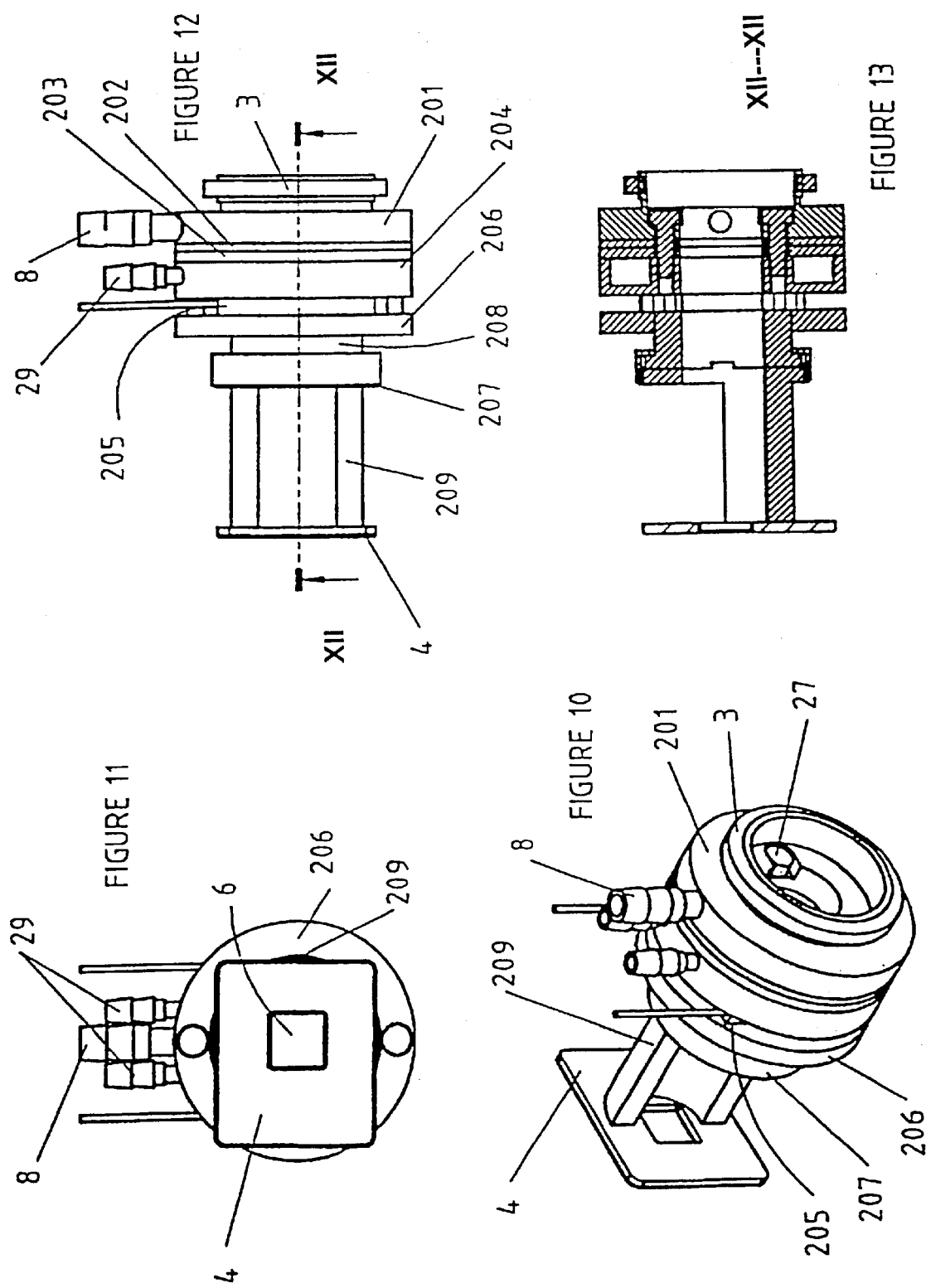

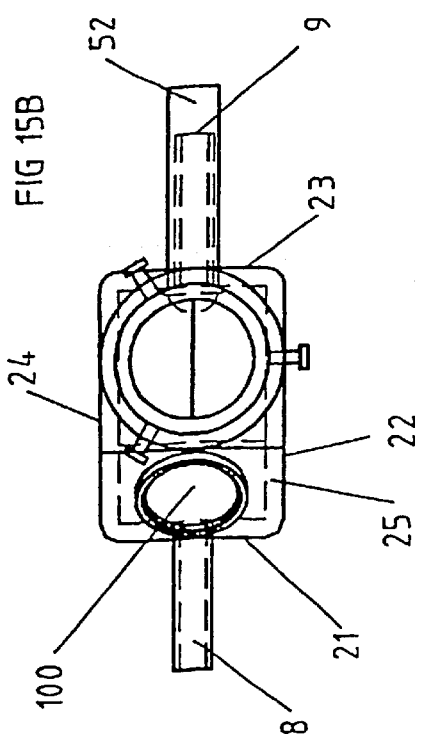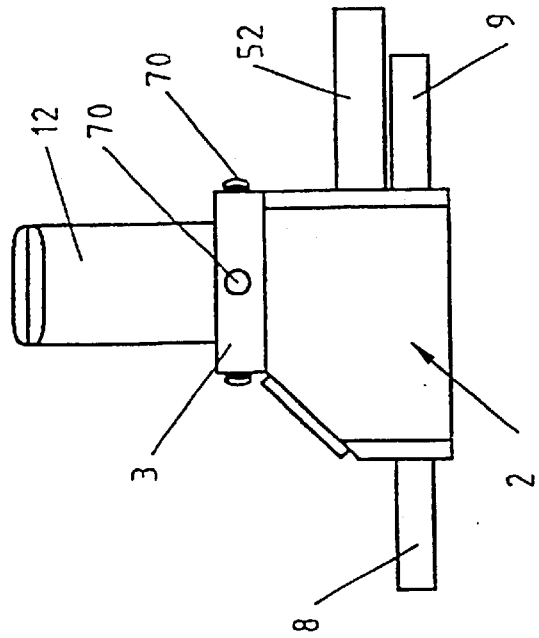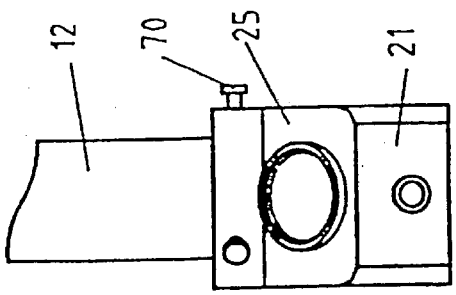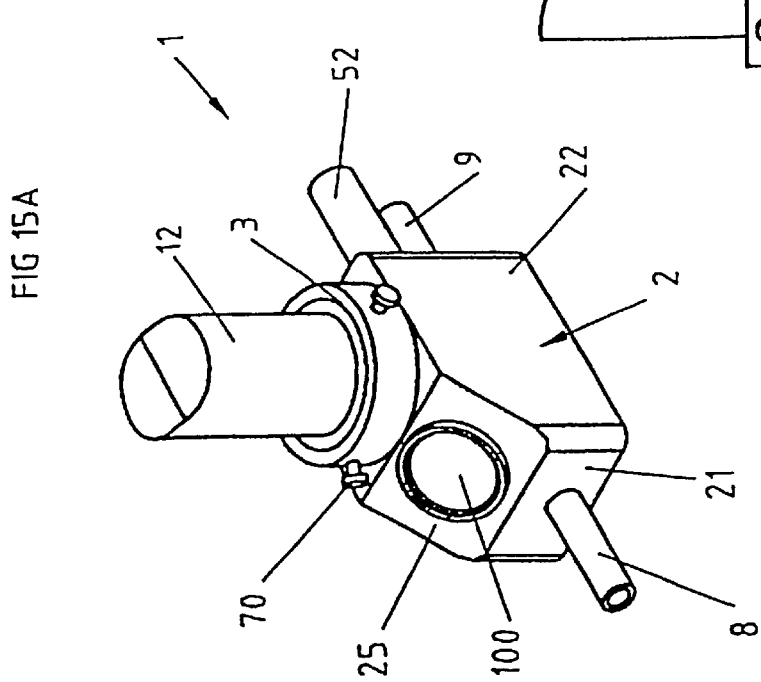

LASER TREATMENT COOLING HEAD

The present invention relates generally to means of cooling the surface of skin during laser treatment (for example, for so-called laser resurfacing), the aim being to reduce the sensitivity to pain, reduce the need for anaesthetic or both. More particularly, the present invention relates to a laser treatment cooling head and, particularly, to a cooling head which can be used with a $CO_2$ or other laser employed for laser treatment of a patient's skin.

The advent of easily usable laser equipment has led to a great increase in this kind of treatment, but the problem of the control of pain, which can be severe as the process is essentially one of burning away skin, remains an obstacle to the wider use of the technique. In particular, according to clinical judgment and patient tolerance of pain, a general or local anaesthetic may be necessary. The use of a general anaesthetic enables the clinician to proceed rapidly with the treatment without constant checking of the comfort of the patient, but carries the severe drawbacks of the well known trauma of general anaesthetics, including the risk and the need for a recovery time before the patient resumes normal life, the need for an anaesthetist and the time for preparation and recovery. The latter two, in particular, make the cost of the treatment very high. In contrast, use of a local anaesthetic can allow a dermatologist to administer the anaesthetic, but again there are drawbacks. Pain control over certain areas of the body, particularly the face, requires multiple injection sites which is traumatic for the patient and the need for top-up doses during treatment is also unpleasant for the patient, also slowing down the treatment. The total dose of local anaesthetic is also limited which can therefore limit a particular treatment session, thus requiring further sessions and associated increased cost.

It has been proposed to use localised cooling to overcome the problems of anaesthesia and, in particular, it has been proposed to utilise a flow of coolant through a laser-transparent glass chamber which can be held against the skin while the laser treatment is carried out. However, this is only possible with visible light lasers, not with $CO_2$, Erbium YAG (yttrium aluminium garnet), or Holmium lasers, as existing cooling devices use coolants and windows that are not lucent to the wavelengths of $CO_2$, Erbium YAG, or Holmium radiation, i.e. current cooling devices using water would absorb the energy at these wavelengths so skin treatment would be impossible.

According to a first aspect of the present invention, there is provided a cooling head for a skin treatment laser, the cooling head comprising a metal or other thermally conductive body having
  a mount disposed at one end for attachment to a laser head to secure the metal body relative to the head in a fixed position;
  a cooling surface at the other end for application to a patient's skin and having an aperture therethrough;
  a bore extending from the mount through the body to the aperture in the cooling surface to allow a laser beam to be passed therethrough to a treatment area of the patient's skin;
  an extraction port for enabling removal of debris from the treatment area and for connection to a vacuum source; and
  an optically transparent window disposed in the body to allow the treatment area at the aperture in the cooling surface to be viewed by a surgeon using the laser; and
a cooling means provided in or on the body to enable heat removal from the body in use in order to cool the cooling surface.

The cooling means may be a coolant passage for example or an electronic cooling means such a Peltier device. For increased flexibility of use, both may be incorporated and used together or separately, say at different times during treatment.

Using a metal body enables a relatively large mass of cold material to be provided as, in effect, a store of refrigerated material, ensuring that cooling around the treatment area can be maintained with a high degree of certainty. The mount may be integral with or separate to the metal body itself.

The optically transparent window disposed in the body may, at its simplest, be provided by simple open section, slot, bore or other aperture in the side wall of body which may be angled towards the aperture in the cooling surface or otherwise provide a line of sight to the aperture. For example, the body may be substantially C or U-shaped in cross-section, ie part of the side wall being either removed or else being left out during manufacture to allow direct vision of the inside of the body and the treatment area, in which case, the aperture at the other end of the body may be co-extensive with the window. In an alternative construction the optically transparent window may be solid, eg glass, and may be a lens.

Preferably, when a coolant passage is employed, it comprises one or more coolant pathways either formed through the metal body or disposed on the exterior of the metal body in intimate contact with the body, to form a heat exchanger. For example, the coolant passage may comprise a helically wound copper tube soft-soldered in contact with a brass body. The coolant may be simply water, brine or another liquid refrigerant and is preferably designed to maintain the cooling surface, ie the contact point of the cooling head with the patient's skin, at a temperature of between $-20°$ C. and $+4°$ C., which temperature may be arranged to be adjustable. However, in an alternative construction, the pathways for coolant may be provided directly within the metal body and the coolant may be a low temperature, laser lucent, gas such as nitrogen (which is lucent to $CO_2$, Erbium YAG, or Holmium laser wavelengths), in which case the nitrogen may be provided to the central bore and may be removed through the extraction port together with debris, by a suitable vacuum pump or the like.

Particularly in constructions where the coolant flows within the head, feedback temperature control of the head may be provided so that the surgeon can set a temperature which is a compromise between the feeling of discomfort from the cold and the laser. The temperature range available should be $-20°$ C. to $+4°$ C. The feedback system may comprise one or more temperature sensors in the head so that the temperature or flow rate or both of the coolant can be adjusted to maintain the desired temperature. For convenience the temperatures of one or more sites in the head can be displayed electronically to the surgeon.

Providing an extraction port to allow extraction of debris and debris vapour reduces the risk of pollution of the treatment area with debris vapour.

According to a second aspect of the present invention, there is provided a cooling head for a skin treatment laser, the cooling head comprising a body having
  a mount disposed at one end for attachment to a laser head to secure the body relative to the head in a fixed position;
  a surface at the other end for application to a patient's skin and having an aperture therethrough;
  a coolant passage through the body to enable a fluid coolant to be passed to a treatment area of the patient's skin through the surface, in use in order to cool the patient's skin;

an extraction passage through the body for enabling removal of coolant and debris from the treatment area;

a bore or passage extending from the mount through the body to the aperture in the cooling surface to allow a laser beam to be passed therethrough; and an optically transparent window disposed in the body to allow the treatment area at the aperture in the surface to be viewed by a surgeon using the laser.

In a first embodiment, the coolant passage connects with the aperture in the surface to enable coolant to be provided to the patient's skin at the point of application of the laser beam. This is preferably achieved by forming the surface of the body simply from the contiguous end faces of a sidewall or sidewalls, defining the sides of a chamber which forms the coolant passage, so that the aperture is provided as the open end of the chamber between the sidewall end faces.

In a second embodiment, the coolant passage passes through the body and the surface at a location adjacent the aperture to enable coolant to be provided to the patient's skin adjacent the point of application of the laser beam.

In both cases, the body may be at least partly formed of metal adjacent the surface in order to enable the surface to be cooled by the flow of coolant through or around the body so as to provide an additional measure of cooling to the patient's skin by the application of the cooled surface to the skin.

A $CO_2$ laser would be incapable of use with the prior art systems mentioned above and therefore the present invention enables the direct application of, for example, $CO_2$, Erbium YAG, or Holmium laser energy to the skin, whilst ensuring that both satisfactory cooling and required visibility for the surgeon are maintained.

The optically transparent window disposed in the body may be provided by a windowed aperture in an angled side wall of body facing towards the aperture in the cooling surface. The optically transparent window may be solid, eg glass and may be in the form of a lens to magnify the treatment area.

Preferably the mount comprises an annular counter-bore at the open end of the bore and has fastenings for securing a laser head in a defined position within the counter-bore.

The surface applied to the patient's skin may be substantially flat or significantly curved, depending on the precise application, ie the particular area of the skin to be treated. For example, when treating significantly concave areas of the skin, such as adjacent the nose, a convex surface in necessary in order that as much of the surface as possible can engage the skin to provide an effective seal with the skin.

Preferably, the coolant passage according to the second aspect of the invention, comprises inlet and outlet ports and an internal chamber formed within the body and opening to the patient's skin through the surface. The coolant may be a low temperature gas such as nitrogen which may be removed through the extraction port together with debris, by a suitable vacuum pump or the like.

A light may be provided within the chamber to illuminate the treatment area.

Various examples of cooling heads according to the present invention will now be described with reference to the accompanying drawings in which.

FIGS. 7A–D show views of the assembled modified head from different positions

Figure 4:
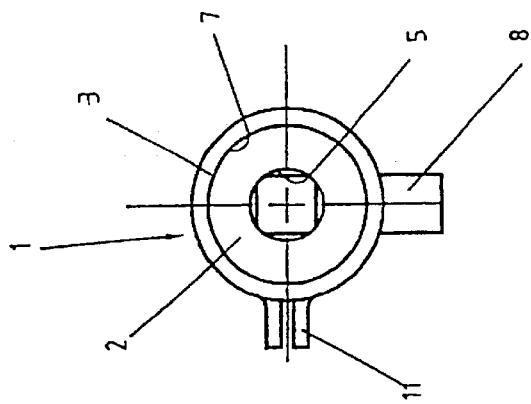
FIGS. 3 and 4 are end elevations on FIG. 1.
Figure 5:
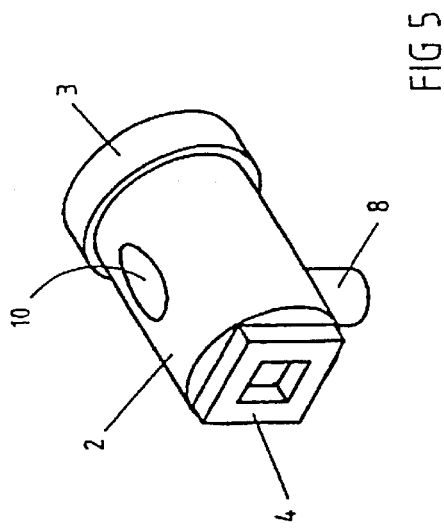
FIG. 5 is an isometric view with the coolant pipe removed.
Figure 1:
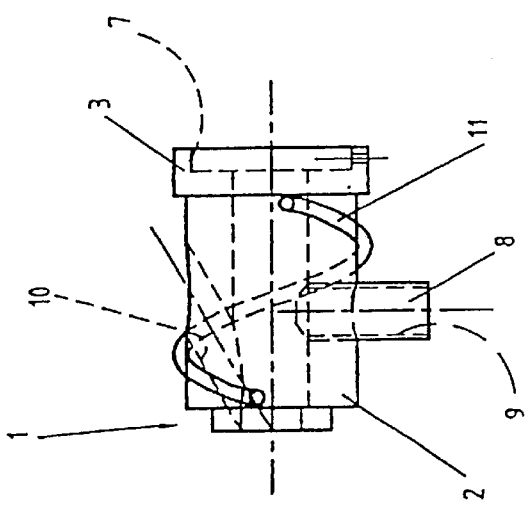
FIG. 1 is a first side elevation of a first cooling head.
Figure 2:
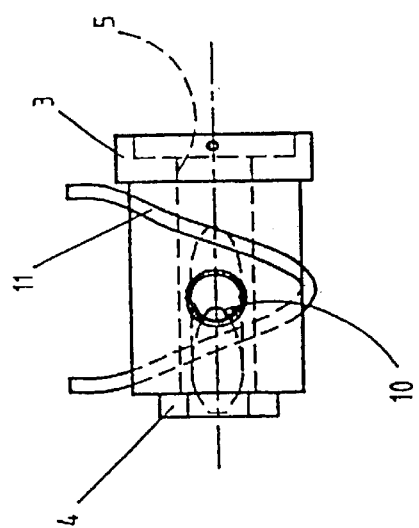
FIG. 2 is a second side elevation at 90° to the first.
Figure 3:
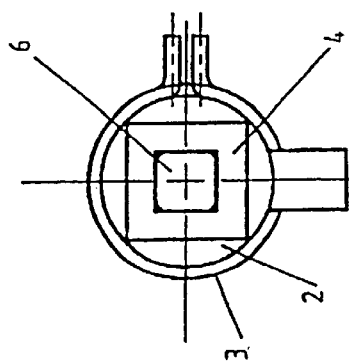
Figure 6:
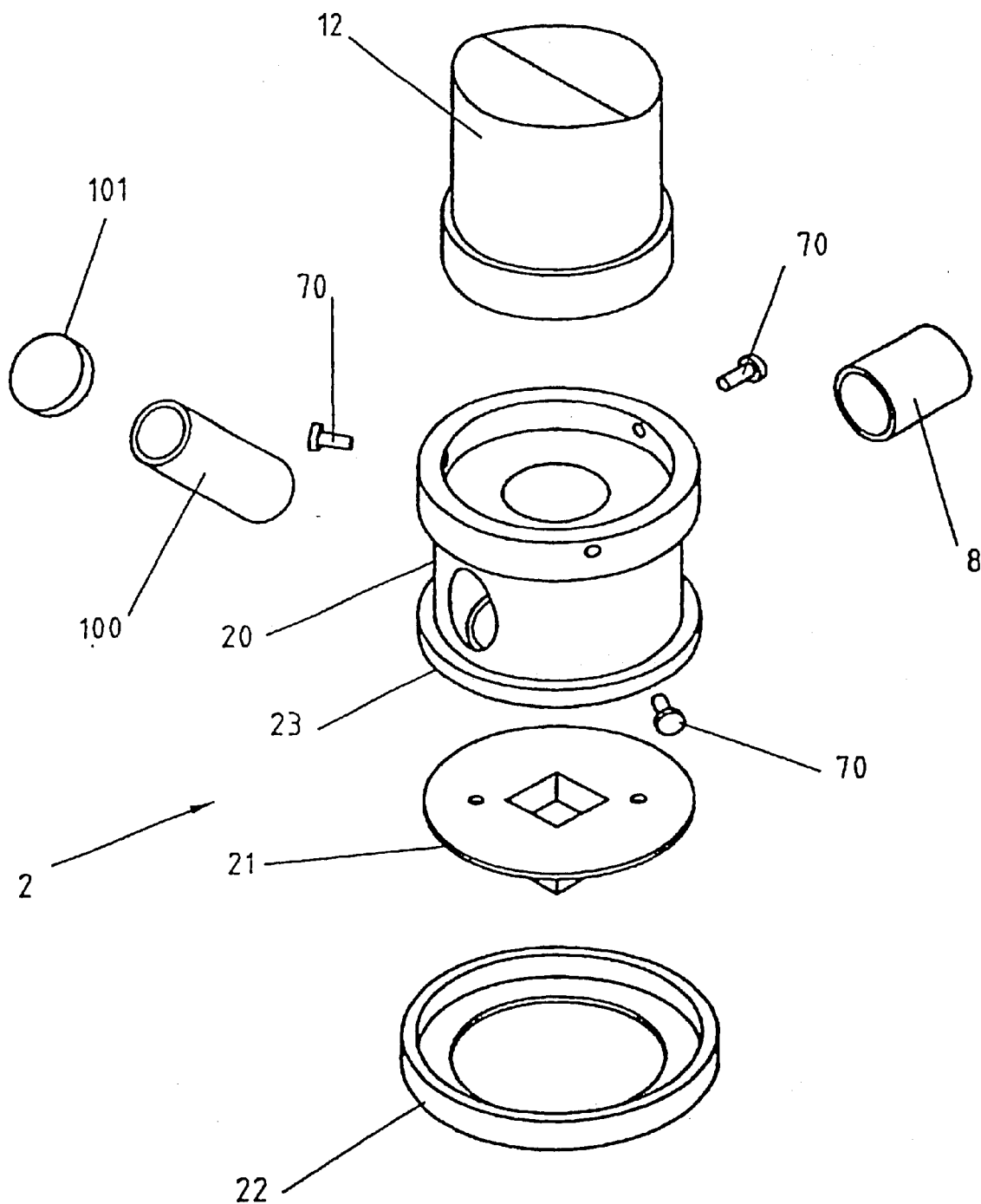
FIG. 6 is an exploded view of a modification of the example shown in FIGS. 1 to 5.
Figures 8, 8A:
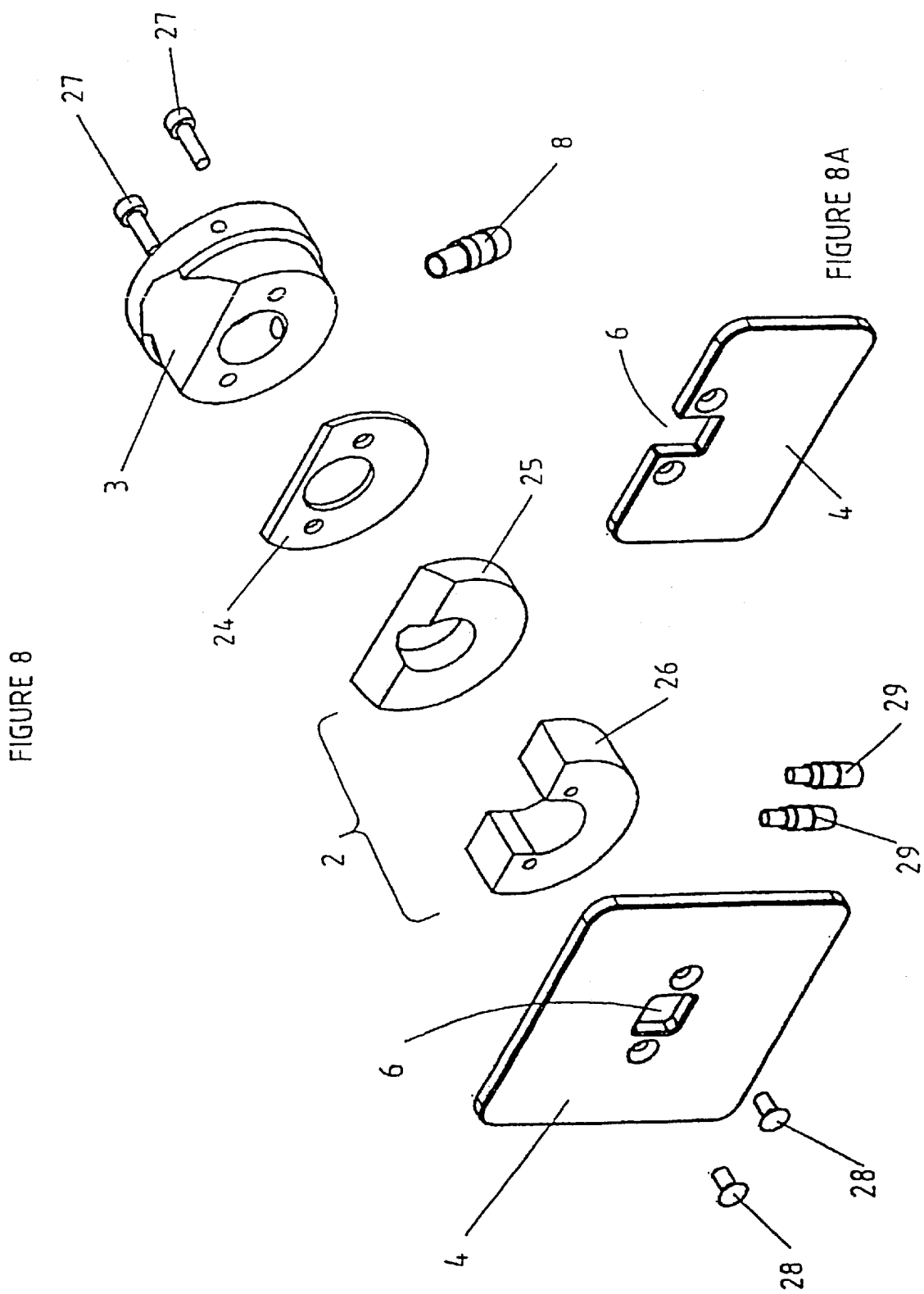
Figure 9:
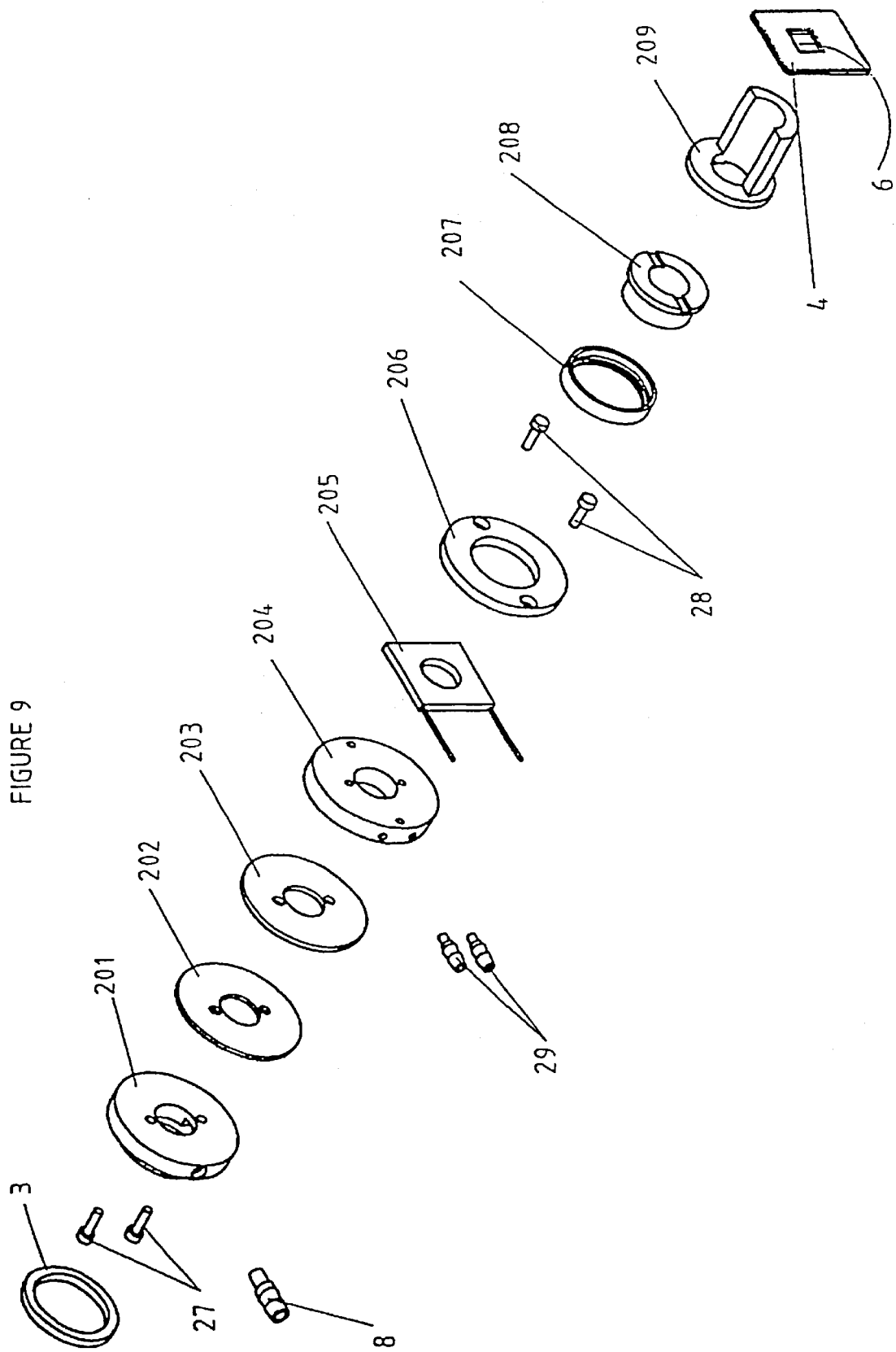
Figure 14:
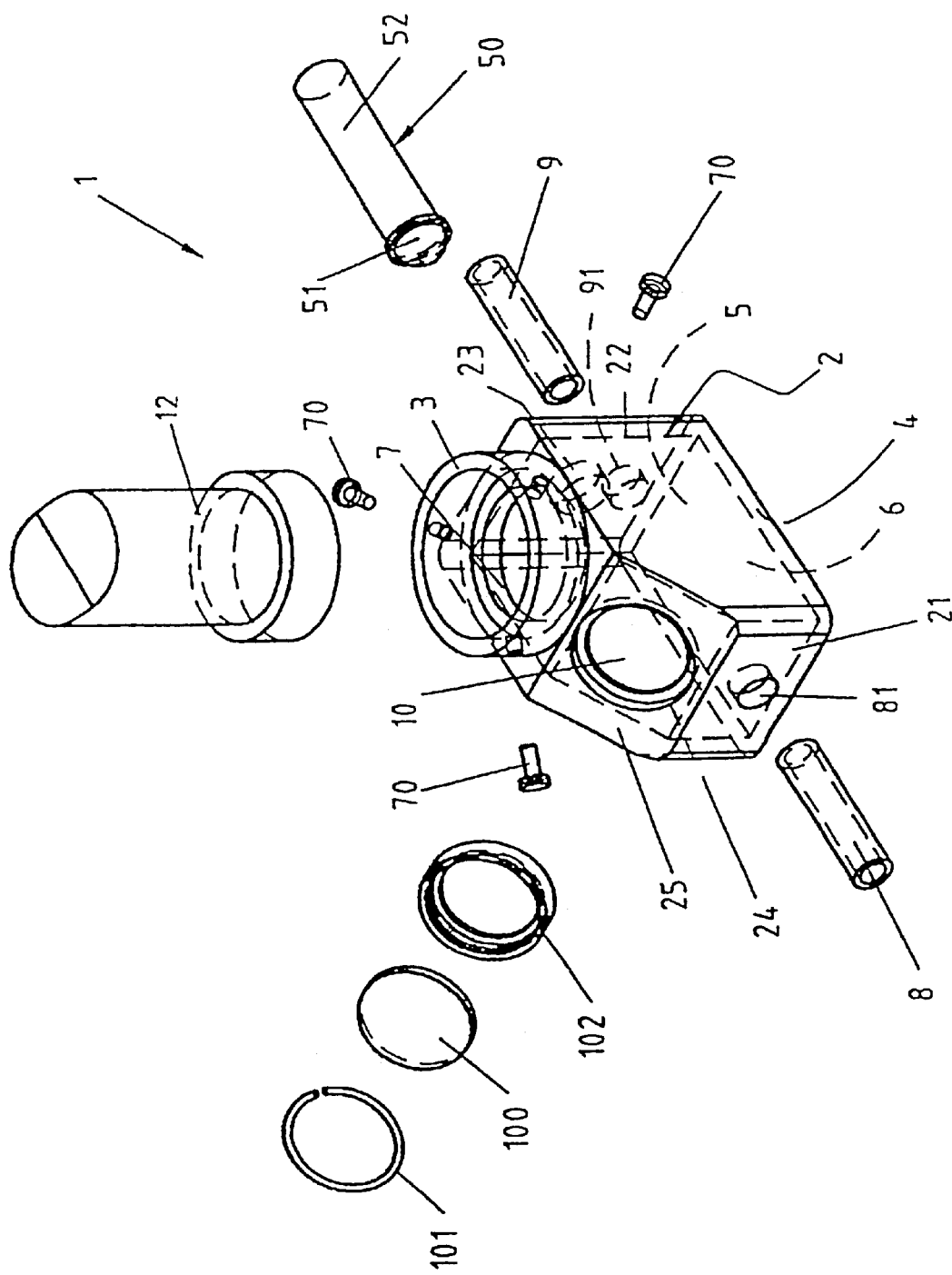

FIG. 8 is an exploded view of a further, third, variant;

FIG. 8A is an isometric view of an alternative contact head for the third variant;

FIG. 9 is an exploded view of a fourth example;

FIGS. 10 to 13 are perspective, end, side and longitudinal section views of the fourth example;

FIG. 14 is an exploded view of a fifth example; and

FIGS. 15A–D show views of the assembled fifth head from different positions.

The cooling heads 1 shown in FIGS. 1 to 7 of the drawings comprises a generally cylindrical brass body 2 having, at one end, a laser mount 3 in the form of an enlarged annular lip and, at the other end, a square-sectioned cooling surface 4. Disposed along the longitudinal axis of the cylindrical body 2 is a bore 5 which extends through the cooling surface 4 at a square aperture 6 and which extends through the annular lip forming the mount 3 within which there is formed a counter-bore 7 of diameter greater than the bore 5 for accurate and secure location of the lower end of a laser housing (not shown).

A brass tube 8 is soft-soldered into a side bore 9 to provide for extraction of debris in use, and an inclined bore 10 which provides a viewing window, extends through the wall of the body 2 on the side opposite the tube 8. As can be seen best from FIGS. 1 and 2, the inclined bore 10 is directed towards the aperture 6. This enables the surgeon to view the area of skin being treated whilst treatment is actually taking place. Helically wound around the cylindrical brass body 2 is a copper pipe or tube 11 through which a refrigerant is passed in order to achieve cooling of the body 2.

In use, the body is pre-cooled my means of the flow of refrigerant through the tube 11, whilst attached to the laser head through the mount 3, and the cooling surface 4 is then applied to the skin of the patient to cool the area of treatment. A suitable vacuum pump attached to the tube 8 is then switched on and the laser actuated as required to treat the skin, debris from the skin being removed through the tube 8. Refrigerant continues to flow through the tube 11 to maintain the body 2 at the desired low temperature in order to desensitise the skin of the patient while the treatment is taking place.

The same reference numerals for component parts are used where appropriate in the drawing of the modification shown in FIGS. 6 and 7A–D and similar parts will not be described again. The modification has a multi-part body 2 which comprises a main part 20 to which is attached a contact head 21, by means of a locking ring 22 secured to a lip 23 on the main part 20, by means of a suitable quick thread or similar for example. This allows different contact heads to be used for application to different areas of the body having different skin curvatures, to enable contact to be maximised and hence cooling optimised.

Such contact heads may include different apertures through which the laser beam passes in use to the skin, e.g., a range of sizes say from 2 to 10 mm may be provided. Additionally, the aperture may be offset from the centre of the head to provide an increased cooling surface on one side, so that increased cooling can be provided in advance of the passage of the laser beam over the treatment area. Different shapes and thicknesses may be utilised to allow treatment of sharply curved areas of skin, eg on the nose.

The head may be anatomically shaped to suit particular areas. The contact head may be articulated to allow the head to move smoothly over anatomical obstacles and contours (eg from cheek to nose) more easily whilst maintaining intimate skin contact. The head may be arranged to rotate, for example, between specific indexed orientations, to enable the direction of traverse to be changed without having to rotate the whole body.

Furthermore, the contact head may be made as a disposable component.

In the modification, the viewing port has a tubular sleeve 100 secured within it, with a transparent window 101 being provided at the free end of the sleeve. The window may be a lens to provide magnification of the treatment site.

Three locking screws 70 serve to locate the lower end of a tubular housing 12 of the laser within the counter-bore 7.

The coolant circuit may be as shown in the first example, or alternatively, may be formed from one or more internal passages in the body 2.

As mentioned, electrical cooling may be provided by controlling the current applied to a Peltier device mounted in the body and this cooling technique may be used alone or in conjunction with fluid cooling.

FIG. 8 shows an exploded view of a third variant in which the mount 3 is separated from the metal body 2 by a plastics or ceramic insulator 24 and the body is formed in two parts 25, 26, the second part 26 of which is C-shaped in cross-section to provide a window in the form of an open side which increases the ability to view the treatment area. The insulator 24 and first body part 25 are chamfered to improve the view through the open side of the body part 26. Fittings 29 provide inlet and outlet ports for fluid coolant to the body part 26 and a port 8 provdes an extraction point for debris. The contact head 4 is in the form of a rectangular plate with a centrally disposed aperture 6. Screws 27, 28 are used to fix the various components together. The modification of the contact head 4 shown in FIG. 8A shows an offset aperture in the form of a slot 6' at one edge of the contact head which, again, is in the form of a plate.

FIGS. 9 to 13 show a fourth example which includes a Peltier electronic cooling device as well as fluid cooling. The construction of this example has a stack of components (similar to the third example) which include a clamping ring 3 providing a mount for the laser tube (not shown). The body 2 has plural component elements 201–209 which are held together by screws 27, 28. An insulating body part 201 has an extraction port 8, supports the clamping ring 3, and sits between it and three heat sink components 202–204. Coolant ports 29 attach to the heat sink 204. A Peltier device 205 (with a central hole to permit the unimpeded passage of laser radiation to the skin) lies adjacent to the component 204 and is clamped to it by a clamping plate 206. A locking ring 207 is captured between the clamping plate 206 and a flanged sleeve 208 which is soldered to the clamping plate 206. An open-sided spacer sleeve 209 to which a contact plate 4 is soldered is attached to the other body parts via the locking ring 207. This example allows either or both of a Peltier and fluid cooling to be used at different times during the treatment process, for example, it may be useful to pre-cool the device by means of the fluid cooling system and then operate the Peltier system during the actual treatment process itself while the head is applied to the skin of the patient. FIG. 13 shows that this construction provides a 35° viewing angle A for the surgeon.

The cooling head 1 shown in FIGS. 14 & 15A to D comprises a generally box-like die-cast or injection moulded body 2 having an annular mounting lip 3 on its top and at the other end a square-sectioned cooling surface 4 formed by the contiguous end faces of sidewalls 21–24 of the body with an aperture 6 formed between the end faces of the sidewalls 21–24. Within the body 2 is a chamber 5 which extends from the annular lip, connecting with it through a bore or passage 7, and being open at the bottom through the end surface 4.

The annular lip 3 provides for accurate and secure location of the lower end of a laser housing 12, three locking screws 70 serving to locate the lower end of the tubular housing 12 for the laser within the bore or passage 7.

A pair of tubular coolant ports 8, 9 are fixed to the sidewalls 21, 23 respectively at corresponding apertures 81, 91 to provide for the inflow and outflow of coolant to the chamber 5, the outlet port 9 also providing for extraction of debris in use.

An inclined bore sidewall 25 has a circular aperture 10 into the chamber 5, which thus provides for a viewing window. Within the aperture 10 is fitted a lens 100, held in place by a circlip 101 and sealed to the side of the aperture with an O-ring synthetic rubber seal 102. The aperture 10 is directed towards the aperture 6 to enable the surgeon to view, with slight magnification, the area of skin being treated whilst treatment is actually taking place.

In use, the body is pre-cooled by means of the flow of refrigerant through the chamber 5 (which may be augmented by an electrical cooling device such as a Peltier), whilst attached to the laser head housing 12, and is then applied to the skin of the patient to cool the area of treatment, debris from the skin being removed through the tubular outlet port 9 togther with spent coolant, which may be filtered and re-cooled for re-circulation through the chamber 5.

To increase visibility of the treatment area, a light 50 can be provided inside the chamber 5, by means of a suitable LED 51 mounted on a tube 52 extending into the chamber through an aperture 53 in the sidewall 23.

What is claimed is:

1. A cooling head for a skin treatment laser, the cooling head comprising
    a metal or other thermally conductive body having
        a mount disposed at one end for attachment to a laser head to secure the body relative to the head in a fixed position;
        a cooling surface at the other end for application to a patient's skin and having a aperture therethrough;
        a bore extending from the mount through the body to the aperture in the cooling surface through respective open ends to allow a laser beam to be passed therethrough to a treatment area of the patient's skin;
        an extraction port for enabling removal of debris from the treatment area and for connection to a vacuum source; and
        an optically transparent window disposed in the body to allow the treatment area at the aperture in the cooling surface to be viewed by a surgeon using the laser; and
        a cooling means provided in or on the body to enable heat removal from the body in use in order to cool the cooling surface.

2. A cooling head according to claim 1, wherein the cooling means comprises a coolant passage.

3. A cooling head according to claim 2, wherein the coolant passage comprises one or more coolant pathways formed through the body or disposed on the exterior of the metal body in intimate contact with the body, to form a heat exchanger.

4. A cooling head according to claim 1, wherein the cooling means comprises an electronic cooling means.

5. A cooling head according to claim 4, wherein the electronic cooling means comprises a Peltier device.

6. A cooling head according to claim 1, wherein the body has a side wall, and the optically transparent window disposed in the body comprises an open section in the side wall of the body.

7. A cooling head according to claim 6, wherein the open section comprises an aperture, said aperture being angled towards the aperture in the cooling surface.

8. A cooling head according to claim 1, wherein the optically transparent window disposed in the body comprises a solid transparent element.

9. A cooling head according to claim 1, wherein the mount has an annular counter-bore at the respective open end of the bore and has fastenings for securing a laser head in a defined position within the counter-bore.

10. A cooling head for a skin treatment laser, the cooling head comprising
   a body having
      a mount disposed at one end for attachment to a laser head to secure the body relative to the head in a fixed position;
      a surface at the other end for application to a patient's skin and having an aperture therethrough;
      a coolant passage through the body to enable a fluid coolant to be passed to a treatment area of the patient's skin through the surface, in use in order to cool the patient's skin;
      an extraction passage through the body for enabling removal of coolant and debris from the treatment area;
      a bore or passage extending from the mount through the body to the aperture in the cooling surface to allow a laser beam to be passed therethrough; and
      an optically transparent window disposed in the body to allow the treatment area at the aperture in the surface to be viewed by a surgeon using the laser.

11. A cooling head according to claim 10, wherein the coolant passage connects with the aperture in the surface to enable coolant to be provided to the patient's skin at the point of application of the laser beam.

12. A cooling head according to claim 11, wherein the body is at least partly formed of metal adjacent the surface in order to enable the surface to be cooled by the flow of coolant through or around the body.

13. A cooling head according to claim 10, further comprising an electronic cooling means.

14. A cooling head according to claim 13, wherein the electronic cooling means comprises a Peltier device.

15. A cooling head according to claim 10, wherein the body has a side wall, and the optically transparent window disposed in the body comprises an open section in the side wall of the body.

16. A cooling head according to claim 15, wherein the open section comprises an aperture, said aperture being angled towards the aperture in the cooling surface.

17. A cooling head according to claim 10, wherein the optically transparent window disposed in the body comprises a solid transparent element.

18. A cooling head according to claim 10, wherein the coolant passage passes through the body and the surface at a location adjacent the aperture to enable coolant to be provided to the patient's skin adjacent the point of application of the laser beam.

19. A cooling head according to claim 10, wherein the coolant passage comprises inlet and outlet ports and an internal chamber formed within the body and opening, to the patient's skin, through the said surface.

20. A cooling head according to claim 10, wherein the mount comprises an annular counter-bore at the respective open end of the bore and has fastenings fro securing a laser head in a defined position within the counter-bore.

21. A method of cooling an area of a patient's skin surrounding a treatment area to reduce or eliminate pain, or tissue damage around the treatment area during skin surgical treatment thereto, the method comprising the steps of:
   applying a cooling surface to a patient's skin, the cooling surface having an aperture therethrough to allow treatment to be effected therethrough to the treatment area of the patient's skin;
   passing a cooling fluid into thermal contact with the cooling surface the cooling fluid being isolated from the treatment area; and
   thereby cooling the cooling surface whereby the area of the patient's skin surrounding the treatment area is cooled.

22. A method of surgical skin treatment, the method comprising the steps of
   applying a cooling surface to an area of a patient's skin surrounding a treatment area, the cooling surface having an aperture therethrough to allow treatment to be effected therethrough to the treatment area of the patient's skin;
   passing a cooling fluid into thermal contact with the cooling surface the cooling fluid being isolated from the treatment area,
   thereby cooling the cooling surface whereby the patient's skin is cooled around the aperture; and
   simultaneously with said cooling, carrying out a surgical skin treatment procedure to the treatment are of the patient's skin through the aperture,
   whereby pain, or tissue damage around the area of treatment are reduced or eliminated by the action of cooling the patient's skin around the area of treatment.

23. A method of cooling an area of a patient's skin surrounding a treatment area during skin surgical treatment to reduce or eliminate pain, or tissue damage around the treatment area, the method comprising the steps of:
   applying a cooling surface to a patient's skin, the cooling surface having an aperture therethrough to allow treatment to be effected therethrough to allow treatment to be effected therethrough to the treatment area of the patient's skin;
   passing a cooling fluid into thermal contact with the cooling surface and to the skin adjacent the cooling surface the cooling fluid being isolated from the treatment area; and
   thereby cooling the cooling surface and the area of the patient's skin surrounding the aperture.

24. A method of surgical skin treatment, the method comprising the steps of:
   applying a cooling surface to an area of a patient's skin surrounding treatment area, the cooling surface having an aperture therethrough to allow treatment to be effected therethrough to the treatment area of the patient's skin;
   passing a cooling fluid into thermal contact with the cooling surface and to the skin adjacent the cooling surface the cooling fluid being isolated from the treatment area;
   thereby cooling the cooling surface whereby the area of the patient's skin surrounding the treatment area is cooled; and
   simultaneously with said cooling, carrying out a surgical skin treatment procedure to the patient's skin through the aperture,
   whereby pain, or tissue damage around the treatment area are reduced or eliminated by the action of cooling the patient's skin surrounding the treatment area.

\* \* \* \* \*